US008175676B2

(12) United States Patent
Chang et al.

(10) Patent No.: US 8,175,676 B2
(45) Date of Patent: May 8, 2012

(54) GENERATING GATING SIGNALS FOR THERMAL THERAPY

(75) Inventors: Hsu Chang, Miaoli County (TW); Win-Li Lin, Taipei (TW); Ming-Chuan Hsu, Taipei (TW)

(73) Assignee: National Health Research Institutes, Miaoli County (TW)

( * ) Notice: Subject to any disclaimer, the term of this patent is extended or adjusted under 35 U.S.C. 154(b) by 683 days.

(21) Appl. No.: 12/241,231

(22) Filed: Sep. 30, 2008

(65) Prior Publication Data

US 2009/0112132 A1    Apr. 30, 2009

Related U.S. Application Data

(60) Provisional application No. 60/976,609, filed on Oct. 1, 2007.

(51) Int. Cl.
*A61B 8/00* (2006.01)
*A61B 6/00* (2006.01)
(52) U.S. Cl. ......................... 600/411; 600/439
(58) Field of Classification Search .............. 706/15–16, 706/41, 45
See application file for complete search history.

(56) References Cited

U.S. PATENT DOCUMENTS

| | | | | |
|---|---|---|---|---|
| 5,553,618 | A | * | 9/1996 | Suzuki et al. ................ 600/411 |
| 5,657,760 | A | * | 8/1997 | Ying et al. ................... 600/439 |
| 6,076,005 | A | | 6/2000 | Sontag et al. |
| 6,621,889 | B1 | | 9/2003 | Mostafavi |
| 6,690,965 | B1 | * | 2/2004 | Riaziat et al. ................ 600/428 |
| 6,735,461 | B2 | * | 5/2004 | Vitek et al. .................. 600/411 |
| 7,171,257 | B2 | * | 1/2007 | Thomson ..................... 600/427 |
| 7,191,100 | B2 | | 3/2007 | Mostafavi |
| 2002/0122702 | A1 | * | 9/2002 | DeBlasio ...................... 408/1 R |
| 2006/0241443 | A1 | * | 10/2006 | Whitmore et al. ........... 600/439 |
| 2007/0055155 | A1 | * | 3/2007 | Owen et al. .................. 600/439 |
| 2008/0146925 | A1 | * | 6/2008 | Byrd et al. ................... 600/438 |

* cited by examiner

*Primary Examiner* — Long V. Le
*Assistant Examiner* — Lawrence Laryea
(74) *Attorney, Agent, or Firm* — Occhiuti Rohlicek & Tsao LLP (57) ABSTRACT

A method of inducing thermal effect at a moving target includes receiving a first data characterizing a repeated motion of the moving target; processing the first data to determine a treatment plan, including determining a plan for directing a signal at the moving target; and controlling the signal directed at the moving target according to the treatment plan to induce a thermal effect.

34 Claims, 12 Drawing Sheets

GENERATING GATING SIGNALS FOR THERMAL THERAPY

CROSS-REFERENCE TO RELATED APPLICATIONS

This application claims the benefit of U.S. Provisional Application No. 60/976,609 filed Oct. 1, 2007. The contents of this priority document are incorporated by reference herein.

BACKGROUND

This invention relates to system and method for generating gating signals for thermal therapy.

High intensity focused ultrasound (HIFU) is a technique that uses high-intensity acoustic power for treating cancer. By inducing local hyperthermia, HIFU causes tissue necrosis in a target region rapidly, e.g., within a few seconds. During a HIFU procedure, a patient's physiological movement, such as respiration, heartbeat, and gastrointestinal peristalsis, can induce motions in the target region and healthy tissues surrounding it. Such motions may affect the precision and effectiveness of the procedure and damage the healthy tissues.

Over the past decade, several approaches have been developed to improve the accuracy and safety of HIFU procedures. One approach, for example, uses image guidance (such as MRI and CT images) to position HIFU transducers when treating a patient. Other approaches include designing multi-dimensional phased-arrays for HIFU transducers, e.g., two or multiple 1-D phased arrays, 1.5-D phased arrays, and 2D phased arrays.

SUMMARY

One aspect of the invention relates to a method of inducing thermal effect at a moving target. The method includes receiving a first data characterizing a repeated motion of the moving target; processing the first data to determine a treatment plan, including determining a plan for directing a signal at the moving target; and controlling the signal directed at the moving target according to the treatment plan to induce a thermal effect.

Embodiments of this method may include one or more of the following features.

The step of processing the first data may include analyzing the first data to determine a trajectory of the repeated motion of the moving target, and may further include using the trajectory of the repeated motion of the moving target to generate an estimate of energy density distribution.

The step of processing the first data may also include using the trajectory of the repeated motion of the moving target to determine a specification of the signal directed at the moving target. The specification of the signal may include a location at which the signal is applied, a duration of the signal, a frequency of the signal, a magnitude of the signal, a timing at which the signal is turned ON or OFF, or a combination thereof.

Each of the first and the second data may include a medical image of the moving target. The medical image may include a MRI or CT image.

The signal directed at the moving target may include focused ultrasound. The step of processing the first data may further include determining a size and a position of a gating window of the focused ultrasound. The step of controlling the signal directed at the moving target may include activating the signal based on a position of the moving target relative to the position of the gating window. The position of the moving target may be detected by a prediction of energy temporal distribution of the focused ultrasound.

The method may further include receiving a second data characterizing the repeated motion of the moving target during application of the treatment plan. The signal directed at the moving target may be controlled based at least in part on a result of processing the second data.

The repeated motion of the moving target may include respiratory motion.

The step of controlling the signal directed at the moving target may include applying a first set of signals at a first element of the moving target to induce a thermal effect on the first element; evaluating the thermal effect on the first element; and, when the thermal effect on the first element satisfies a predetermined criterion, terminating application of the first set of signals on the first element. The step of controlling the signal directed at the moving target may further include applying a second set of signals at a second element of the moving target to induce a thermal effect on the second element.

Another aspect of the invention relates to a system for inducing thermal effect at a moving target. The system includes an interface for receiving a first data characterizing a repeated motion of the moving target; a processor for determining a treatment plan according to the first data, the treatment plan including a plan for directing a signal at the moving target; and a controller for receiving the treatment plan and for controlling the signal directed at the moving target to induce a thermal effect according to the treatment plan.

Embodiments of this system may include one or more of the following features.

The system may further include a source for generating the signal. The source may include a multi-channel ultrasound system.

The signal may include focused ultrasound, and the source may include an ultrasound transducer. The ultrasound transducer may be a multi-dimensional phased array transducer.

The processor is configured to analyze the first data to determine a trajectory of the repeated motion of the moving target. The processor is further configured to estimate an energy density distribution based on the trajectory of the repeated motion of the moving target. The processor may also be configured to determine a position of a gating window of the signal directed at the moving target based on the energy density distribution.

The first data includes a medical image of the moving target. The processor is configured to analyze the first data to estimate an energy density distribution, and may be further configured to determine a position of a gating window of the signal directed at the moving target based on the energy density distribution.

The system may further include a data acquisition system for detecting a position of the moving target during application of the treatment plan.

The data acquisition system may be configured to generate a medical image for detecting the position of the moving target. The data acquisition system may include a MRI system, or alternatively, include a video camera system.

The controller is configured to activate the signal based on a relative position of the moving target with respect to the gating window, and be further configured to activate the signal according to a power activation algorithm. The power activation algorithm may include a training algorithm configured to predict a future position of the moving target based on previously-detected positions of the moving target. The training algorithm may include a network structure including at least an input layer, a hidden layer, and an output layer.

The controller may be configured to activate the signal directed at the moving target based on the prediction of a future position of the moving target. The controller may also be configured to evaluate the thermal effect based on the medical image generated by the data acquisition system.

The repeated motion of the moving target is induced by physiological movement of the moving target, which may include respiratory motion.

Other features and advantages of the invention are apparent from the following description, and from the claims.

DETAILED DESCRIPTION

1 Thermal Therapy Using HIFU

Thermal therapy applies heating techniques to induce localized temperature elevation for treating cancer. One example of thermal therapy relies on focused ultrasound to provide a non-invasive ablation means on human tumor tissues.

Figure 1:
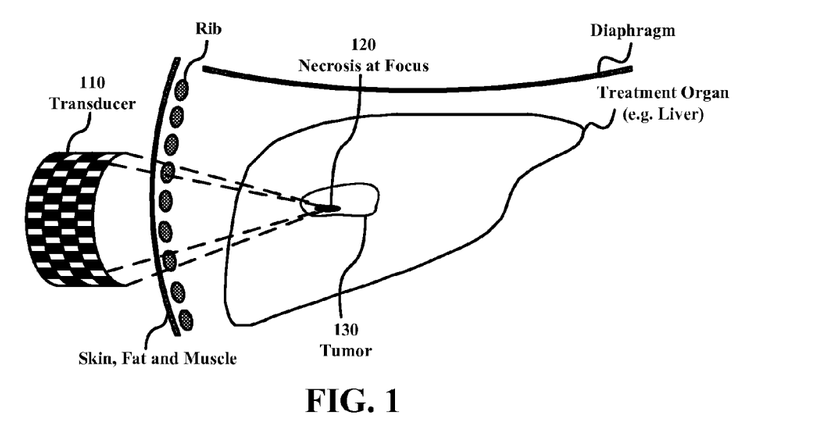
FIG. 1 is a schematic diagram illustrating a thermal therapy technique using high intensity focused ultrasound.

Referring to FIG. 1, in one embodiment of a high-intensity focused ultrasound (HIFU) system, ultrasound signal is delivered via an array of ultrasound transducer 110 (e.g., concave transducer) to a target region 120. One example of such a HIFU system provides a focal distance of 10 cm, and a focal lesion with a length of 20 mm and a cross sectional diameter of 5 mm. The small cross-sectional dimension of the focal lesion allows the ultrasound signal to be focused on target tumors without injuring surrounding tissues.

Figure 2:
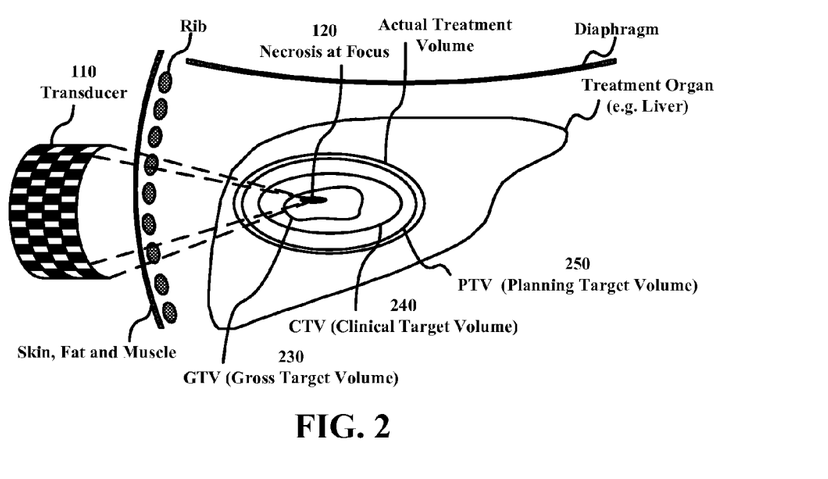
FIG. 2 is a schematic diagram further illustrating the thermal therapy technique shown in FIG. 1 that applies unit definitions adopted by the International Commission on Radiation Units and Measurements (ICRU).

Referring to FIG. 2, one exemplary design of a HIFU treatment is shown. Here, in accordance with the definitions adopted by the International Commission on Radiation Units and Measurements (ICRU) on conventional thermal therapy procedures, three distinct regions are defined within a target organ of treatment (e.g., liver). These regions include a gross target volume (GTV) 230, a clinical target volume (CTV) 240, and a planning target volume (PTV) 250, each described in detail below.

The GTV 230 refers to a tissue volume of the gross palpable or visible/demonstrable extent of malignant growth. The CTV 240 refers to a tissue volume that contains a demonstrable GTV and/or subclinical microscopic malignant disease that needs to be removed. Generally, it is desirable to treat the CTV 240 adequately in order to achieve the goal of therapy, cure or palliation. The PTV 250 refers to a planned tissue volume selected to ensure that the prescribed doses of the focused ultrasound are absorbed in the CTV 240. In other words, the GTV 230 and the CTV 240 contain tissues to be treated, while the PTV 250 includes a margin around the CTV 240 to account for patient movement and uncertainties in treatment set-up. Preferably, the margin of the PTV 250 around the CTV 240 needs to be controlled in order to lower the risk of damaging healthy tissues during treatment.

Figure 3A:
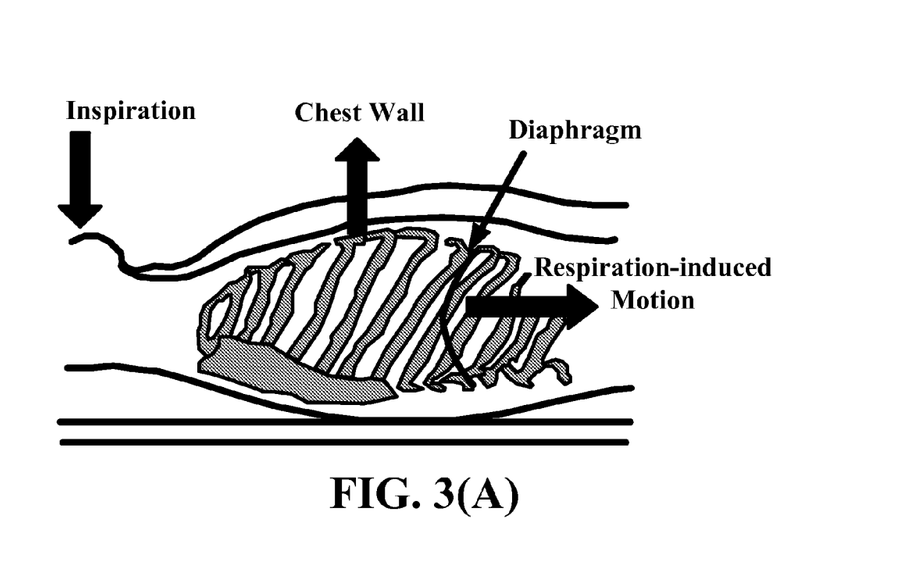
FIG. 3 is a schematic diagram illustrating the respiratory motion of a patient.
Figure 3B:
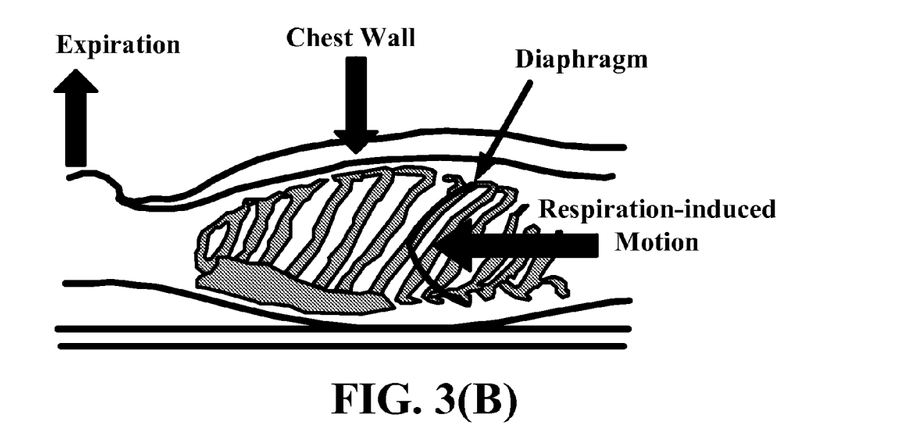

FIG. 3 shows one type of physiological movement of a patient—respiratory motion—that may affect the selection of PTV 250 for thermal therapy. During therapy, a patient's respiratory motion would cause the movement of his heart, kidney, liver, pancreas, and spleen to be up to several centimeters. As a result, the margin of the PTV 250 beyond the CTV 240 is usually selected to be relatively large.

Figure 4:
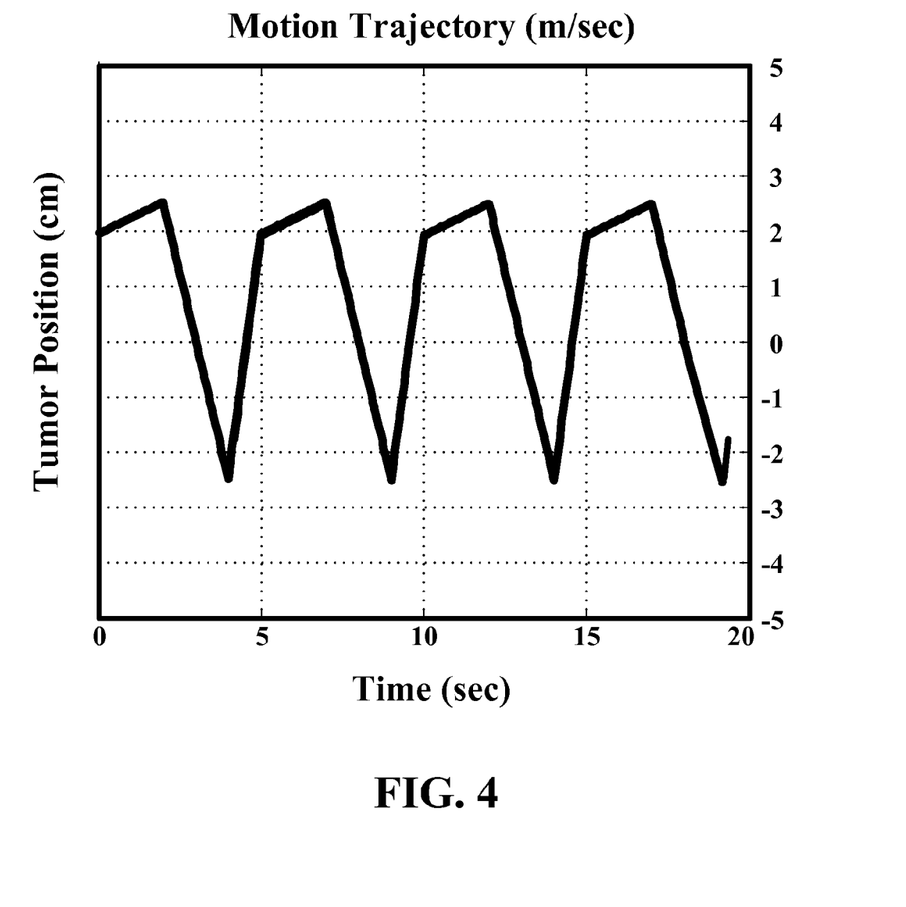
FIG. 4 is a graph showing an exemplary motion trajectory of a tumor.

FIG. 4 shows an exemplary trajectory of a target tumor. Because of the periodic respiration motion, the movement of the tumor and surrounding organs is also periodic. Therefore, the positions of the tumor and organs are predicable. The rib structures, however, move in three dimensions (as shown in FIG. 3), causing the ultrasound interference due to the combined effects of both organ and rib movements to be unpredictable.

During a HIFU procedure, the amount of energy absorbed by each GTV or CTV (and accordingly, the temperature) can be evaluated in the following way.

First, assuming that the energy source (e.g., the transducer 110) delivers energy in the form of continuous wave sonication, the ultrasonic pressure field from multiple point-sources within the transducer can be computed as:

$$P_{pn}(x, y, z) = j\frac{\rho c k}{2\pi}\mu\sum_{n=1}^{N}\sum_{n'=1}^{N'}\Delta x \Delta y \quad (1)$$

where $\rho$ is the tissue density, c is the speed of sound, k is the wave number, $\Delta x$ and $\Delta y$ are the dimensions of a unit grid, and $\mu$ is the ultrasound attenuation coefficient.

Second, based on the ultrasonic pressure field $P_{pn}$ calculated above, to obtain the amount of energy absorbed by a target tissue, the acoustic power deposition q is given as:

$$q = \frac{\alpha P_{pn}^2}{\rho c} \qquad (2)$$

where α is the ultrasound absorption coefficient of the target tissue, $P_{pn}$ is the ultrasonic pressure obtain from equation (1), ρ is the tissue density, and c is the speed of sound in the target tissue.

Third, the temperature distribution within the targets tissue can be obtained using the Pennes' bio-heat transfer equation:

$$\rho c_t \frac{\partial T}{\partial t} = k \nabla^2 T - w_b c_b (T - T_a) + q \qquad (3)$$

where $c_t$ and $c_b$ are the specific heat capacities of the target tissue and blood respectively, k is the thermal conductivity, $w_b$ is the blood perfusion rate, T and $T_a$ are the temperatures of the target tissue and blood respectively, and q is acoustic power deposition obtained from equation (2).

Some exemplary parameter values used in equations (1)-(3) are shown in Table 1.

TABLE 1

| Parameters | Value |
| --- | --- |
| Velocity of Sound, c (m s$^{-1}$) | 1569 |
| Ultrasound Attenuation Coefficient, μ (Np M$^{-1}$ @ 1 MHz) | 4.4 |
| Tissue Density, ρ (kg m$^{-3}$) | 1170 |
| Ultrasound Absorption Coefficient, α (Np M$^{-1}$ @ 1 MHz) | 3.0 |
| Thermal Conductivity, k (W m$^{-1}$ ° C.$^{-1}$) | 0.64 |
| Specific Heat Capacity (tissue/blood), $c_t/c_b$ (J kg$^{-1}$ ° C.$^{-1}$) | 3770 |
| Blood Perfusion Rate, $W_b$ (kg m$^{-3}$ s$^{-1}$) | 10 |

2 Gating Strategy

One approach to reduce motion-induced effects in thermal therapy uses a gating strategy that focuses ultrasound beams into a selected region ("window") and only activates the transducer when a target element (e.g., tumor) appears in the selected window. The size and location of the window are determined, for example, based on the characteristics of human respiratory motion.

Referring to FIGS. 5A-5D, one implementation of the gating strategy is illustrated. Here, an ultrasound transducer 510 is configured to focus ultrasound beams into the range of gating window 530. More specifically, the cross-sectional diameter of the focal spot of the beams is comparable to the size of gating window 530. A PTV 550 has multiple GTV elements 520 that are arranged for treatment in a predetermined order. During the treatment, each GTV element follows the patient's respiration to move along Y-axis, entering and exiting the gating window 530 in cycles. The transducer 510 is powered on and off according to the relative position of the GTV element 520 during each cycle.

Figure 5A:
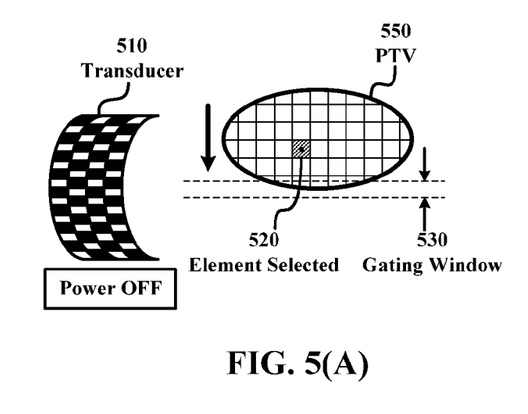
FIGS. 5A-5D are schematic diagrams of generating gating signals during thermal therapy.
Figure 5B:
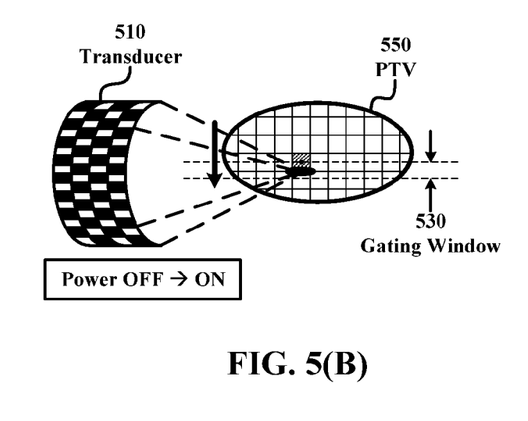
Figure 5C:
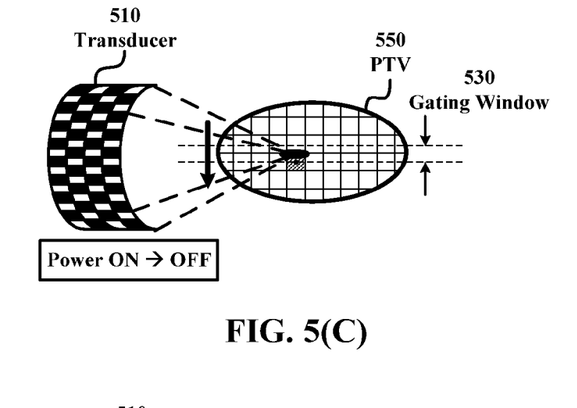
Figure 5D:
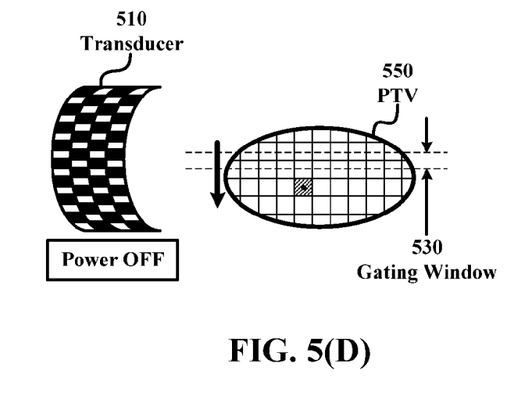

As shown in FIG. 5A, when the GTV element 520 is outside the gating window 530, the ultrasound transducer 510 is turned off. No sonication power is delivered to the GTV element 520, or the PTV 550. As soon as the GTV element 520 enters the gating window 530, the ultrasound transducer 510 is turned on to start treating the element (shown FIG. 5B). When the GTV element 520 travels within the gating window 530, the transducer 510 continues to deliver ultrasound energy (shown in FIG. 5C) until a certain portion or all of the GTV element 520 exits the gating window 530, at which time the transducer 510 is turned off again (shown in FIG. 5D).

Figure 6:
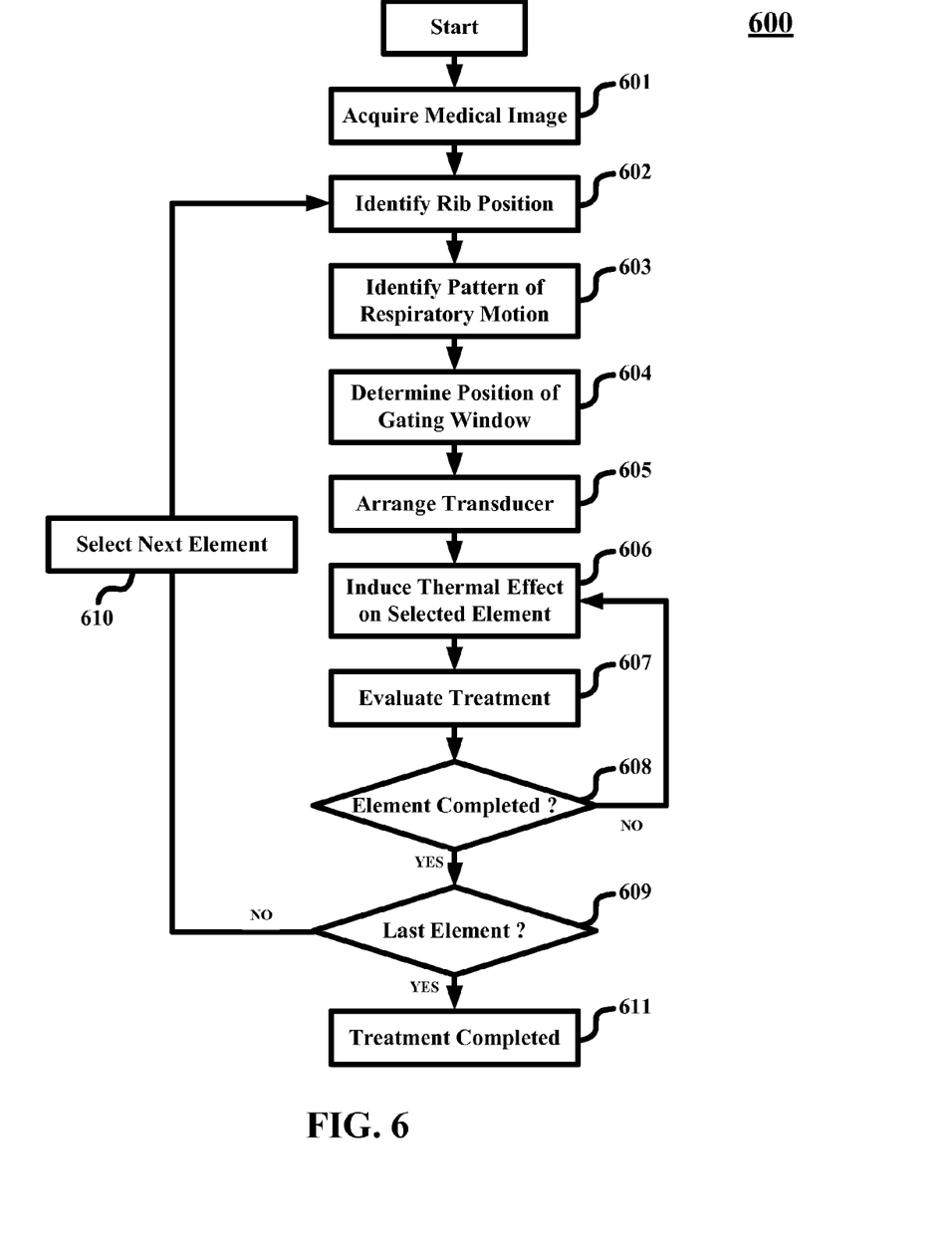
FIG. 6 is a flow chart illustrating a treatment procedure according to one embodiment of the present invention.

Referring to FIG. 6, a flow chart 600 illustrates an exemplary treatment procedure that uses the gating strategy described above.

At the beginning of the procedure (step 601), medical images of a patient are first acquired, for example, via MRI and/or CT imaging. From these medical images, physiological information of the patient, such as the position of rib structures and the pattern of respiratory motion, can be determined (steps 602 and 603).

Next, based on the patient's physiological information, a treatment plan is determined during a planning stage (steps 604 and 605). The treatment plan includes a specification of the gating window and the arrangement (including both the angle and position) of the transducer. Here, the gating window can be determined based on a prediction of energy spatial distribution of a target volume (element), as will be described in greater detailed in a later section.

After the planning stage, in step 605, the position, angle and driving circuits of the ultrasound transducer are arranged according to the treatment plan. Subsequently, the transducer is turned ON to deliver power to the first GTV element of the target volume at selected intervals. The timing at which the transducer is turned ON/OFF is controlled by detecting/predicting the timing at which the GTV element 520 enters/exits the gating window 530 (as illustrated in FIGS. 5A-5D). One way of detecting/predicting the entrance/exit is based on energy temporal distribution, as will be described later.

In parallel to delivering ultrasound energy to the target volume (step 606), the system evaluates the effect of thermal treatment (step 607), for example, using medical imaging techniques such as MRI. For instance, by estimating a temperature or a degree of protein denaturation of the target volume, the HIFU system determines whether a desired treatment effect has been reached on the selected GTV element (step 608). If so, the system selects the next GTV element in the PTV 550 that needs to be treated and iteratively performs the thermal procedures (steps 601 to 608); otherwise, the treatment on the previously selected GTV element continues until the desired effect is reached. Upon completing the treatment on the last GTV element in the PTV 550, the thermal therapy concludes (step 611).

Achieving a good gating strategy for the treatment includes making the following two decisions. First, for a selected target volume, determine the position and the size of the gating window and further, determine the position and arrangement of the transducer. Second, determine when to deliver/interrupt ultrasound power to the selected target volume, for example, by detecting when the target volume is approaching/leaving the gating window.

Figure 7:
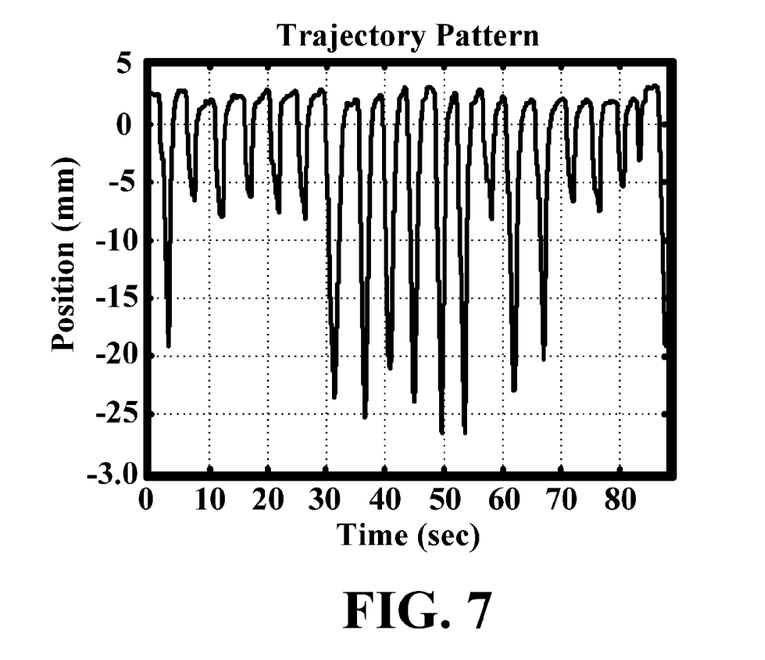
FIG. 7 is a graph showing a motion trajectory of a subject.
Figure 8:
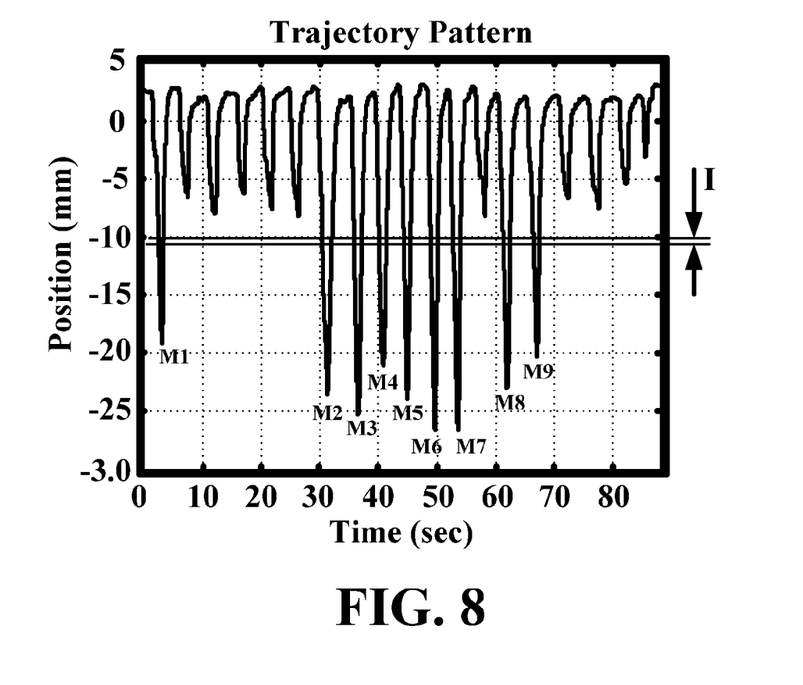
FIG. 8 is a graph showing the calculation of slopes M1 to M9 in the motion trajectory of FIG. 7.
Figure 9:
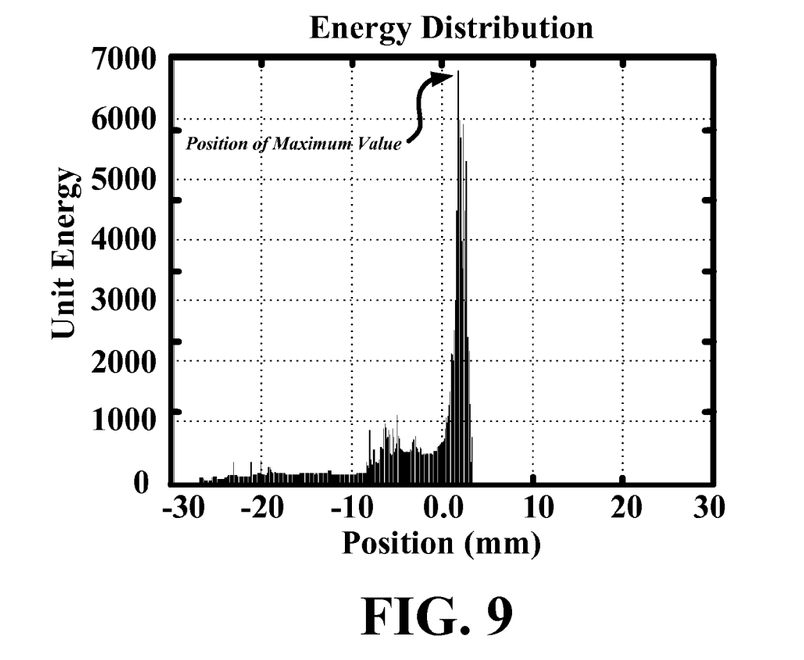
FIG. 9 is a graph showing an energy density distribution obtained from FIG. 8.

Referring to FIG. 7 to FIG. 9, one approach to selecting the position and size of gating window uses energy spatial distribution determined based on tumor trajectory. FIG. 7 shows the trajectory of a subject under the influence of respiratory motion. In this figure, Y axis refers to the position of the target volume and X axis refers to time. In FIG. 8, a thin band "I" is placed in parallel to the X axis near the "−15 mm" position as a reference band. This reference band intersects the trajectory at multiple time locations at which the slope of the trajectory can be determined. For example, as shown in the graph, $M_1$ to $M_9$ respectively represent the slopes of the nine descending/ascending segments of the trajectory that are enclosed in the reference band The energy spatial distribution at each time location can then be determined as follows.

Here, $M_i$ refers to the slope of the ascending or the descending trajectory at the "i-th" intersection. The time period during which the subject's position falls in the reference band at this intersection can be obtained using $d(T_i)=dx/M_i$, where $T_i$ is the sonication time at the "i-th" intersection, and dx is the width of the reference band. Here, the width of the band is selected based on various considerations, including, for example, the selected duty cycle of the transducer, the specification of the hardware components in the system, and the patient-specific treatment plan. The total time along reference band I is thus the sum of $d(T_i)$, where in the example of FIG. 8, i is equal to 1 to 9.

The energy density at the reference band of −15 mm is equal to sonication power times the total length of time that the position of a subject falls within the band.

By shifting the reference band along y-axis and computing the energy density at each y-position, the spatial distribution of energy density can be obtained. Referring now to FIG. 9, energy density is shown as a function of the subject's position. Here, the Y-axis refers to the energy density, computed at each position as the sonication power multiplied by the duration of this position and normalized by a sampling rate (e.g., $\frac{1}{18}$ s). From this figure, the maximum energy absorption by the subject occurs when the subject is near the position of 0 mm.

Figure 10:
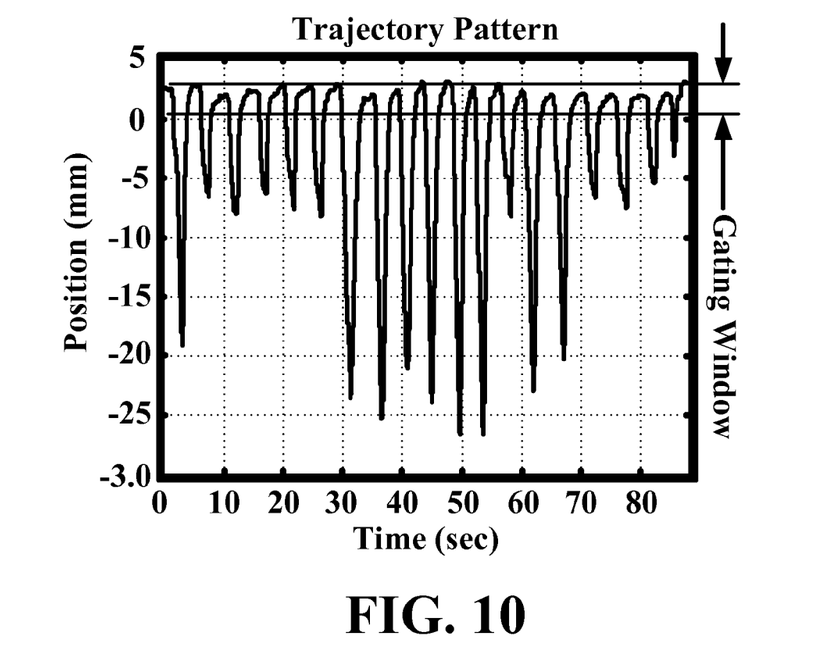
FIG. 10 is a graph showing gating window selection based on the energy density distribution of FIG. 9.

Referring to FIG. 10, based on the energy density distribution shown in FIG. 9, one example of selecting a gating window that can improve treatment efficiency is to select: 1) a window position such that the ultrasound beams is focused into a region of the subject that has the maximum energy density; and 2) a window size such that the size of the focal spot of the ultrasound beams is adjusted to be, for example, approximately the same as the size of a target volume.

In addition to the above-described trajectory-based approach, a second approach to determine the energy spatial distribution uses temperature information of tissues (for example, obtained from MRI). For instance, a color-scaled temperature map of a treatment region imaged by MRI can indicate the level of ultrasound-induced temperature elevation at individual elements of the region. By obtaining a series of temperature maps that each corresponds to the application of a different candidate gating window, the spatial distribution of energy density can be obtained with respect to candidate window positions. The window position that yields the maximum energy absorption can thus be selected to be the one for implementation.

Figure 11A:
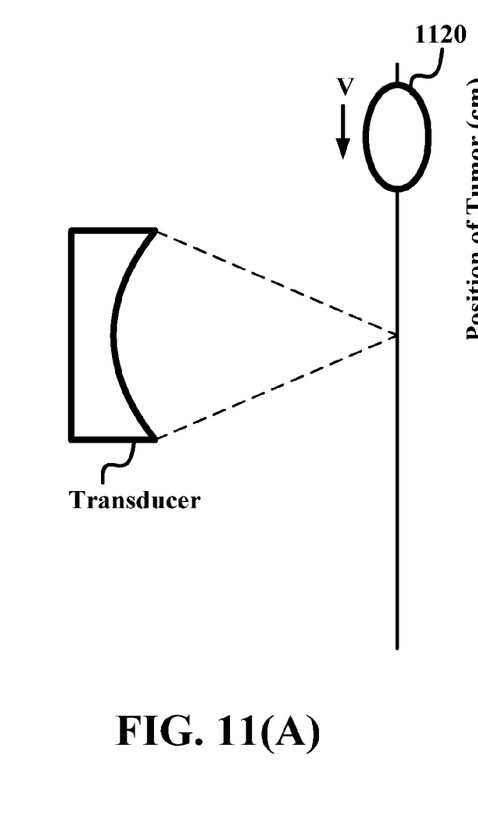
FIG. 11A is a schematic diagram of a target element entering/exiting a gating window.
Figure 11B:
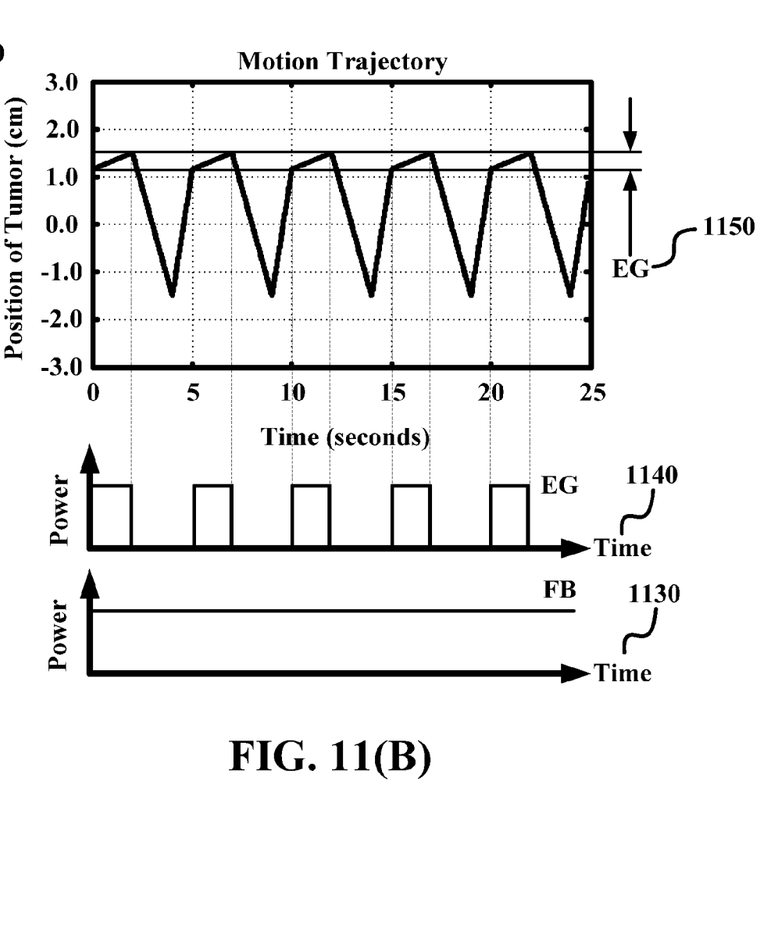
FIG. 11B is a graph showing a sonication power activation algorithm for delivering sonication power at the target element.

Referring now to FIGS. 11A and 11B, one example of applying the gating strategy described with reference to FIGS. 7-10 is illustrated. The tumor trajectory in FIG. 11B is also shown in previously-described FIG. 4. Here, EG refers to a gating window 1150 that is positioned between 0.02 m to 0.03 m along the y-axis. By comparison, FB refers to a traditional procedure during which ultrasound beams are continuously delivered to a selected region without interruption (graph 1130).

As target element 1120 follows respiratory motion, ultrasound power is delivered periodically to the target element 1120 according to the gating window EG. More specifically, in this example, the time interval for each power activation cycle corresponds to the slow mode of tumor motion in each respiratory cycle (graph 1140). During the fast mode of tumor motion when the target element 1120 locates beyond the range of gating window EG, the transducer is turned off to avoid injury to normal tissues.

In many applications, it is useful to control the activation of ultrasound power, for example, based on the relative position of the target volume to the gating window. In some applications, particular system configuration (e.g., using a multiple-channel ultrasound driving system) can lead to time delay in power activation. More specifically, when the actual time of power delivery lags behind the designed activation time, the treatment may not be able to induce the sufficient amount of thermal effect on the target volume, whereas in the mean time, surrounding tissues can be damaged.

One approach to improving power activation control uses a sonication power activation algorithm, which is designed to predict the energy distribution in time domain (also referred to herein as energy temporal distribution).

Figure 12:
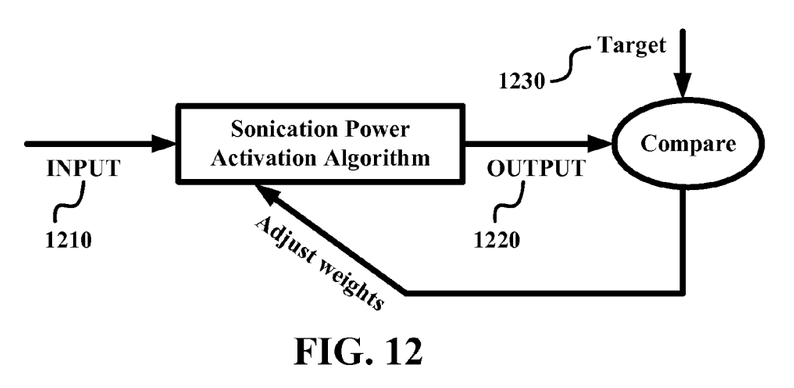
FIG. 12 is a flow diagram of the sonication power activation algorithm shown in FIG. 11.

Referring to FIG. 12, one example of the sonication power activation algorithm is an adjusted/trained activation algorithm. In this example, an output 1220 of an input signal 1210 is compared with a target output 1230. The difference between the output 1220 and the target 1230 is used to adjust weights of the activation algorithm in a feedback loop, so that the output 1220 of the adjusted activation algorithm is equal or close to the target output 1230.

Figure 13:
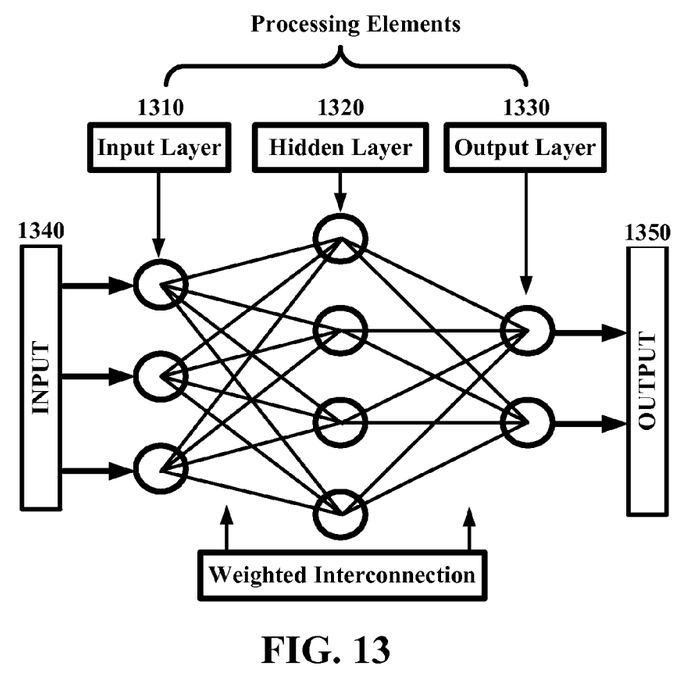
FIG. 13 is a schematic diagram of a network structure of the sonication power activation algorithm shown in FIG. 12.

Referring to FIG. 13, a basic structure of one embodiment of the sonication power activation algorithm is shown. Here, nodes of high correlation connections are used to process data and to respond to external inputs using the trend of the power activation algorithm. Generally, there are three computing layers, including for example: an input layer 1310, a hidden layer 1320 and an output layer 1330. The functions of each layer are described below.

Input layer 1310—Accept external inputs 1340 and prepare signals for processing.

Hidden layer 1320—Receive and process signals from the input layer 1310. The course of the signal processing is invisible to the user of the algorithm.

Output layer 1330—Accept the processed signals of the algorithm and generate outputs 1350.

In another embodiment of the sonication power activation algorithm, a back-propagation neural network technique is used for training the algorithm. More specifically, static back-propagation is used to produce an instantaneous mapping of a static input to a static output. Inputs and the corresponding target outputs are used to train an algorithm until it can approximate a function, and to associate inputs with specific outputs. Properly trained back-propagation algorithm tends to generate reasonable results when presented with inputs that the algorithm has never seen. A new input similar to an existing input used in training typically leads to an output that is also similar to the output of the existing input. This characteristic makes it possible to train an algorithm with a representative set of input/target pairs and to achieve good results without exhaustive training on all possible input/output pairs.

Figure 14:
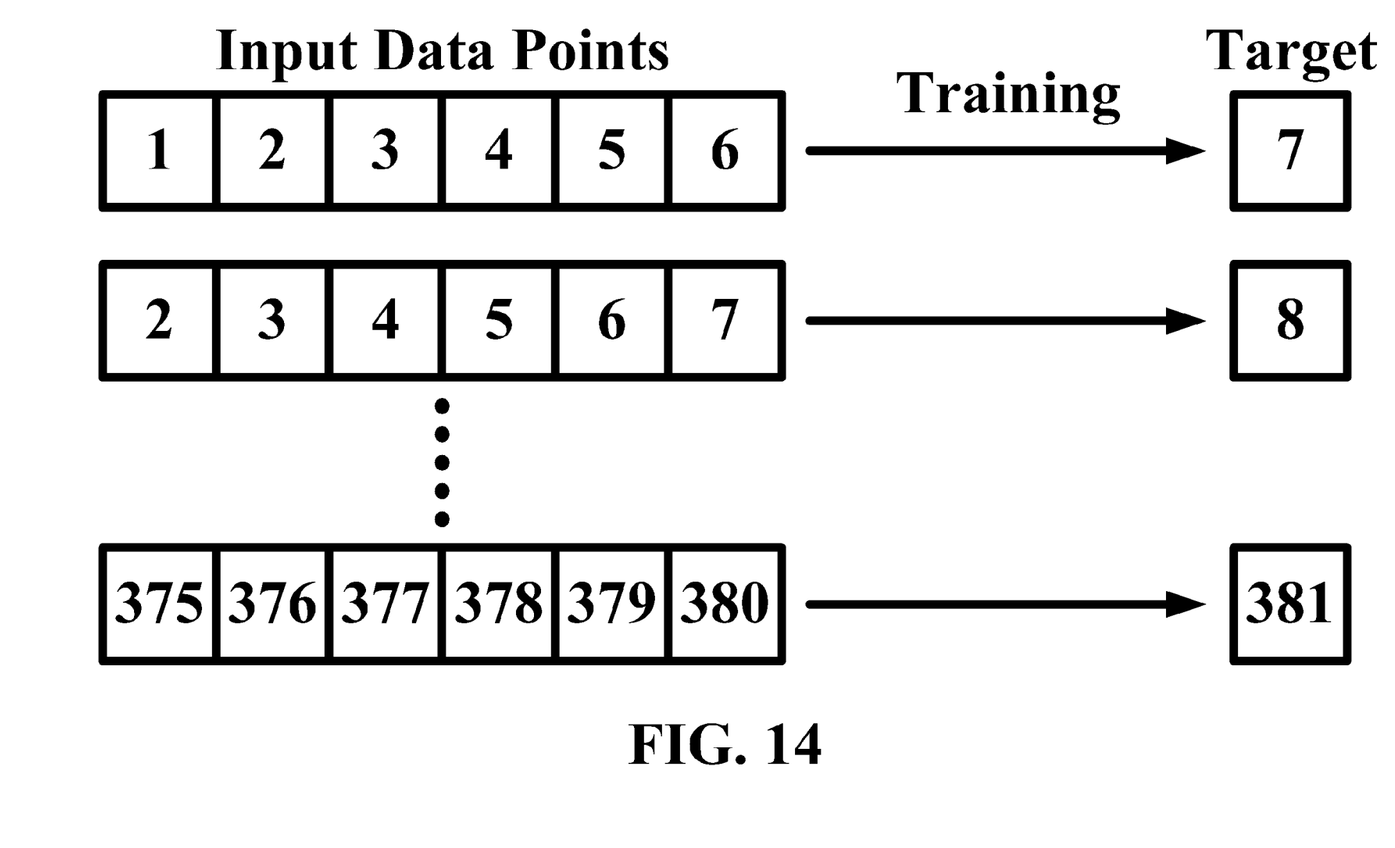
FIG. 14 is a schematic diagram of an exemplary set of training data for the sonication power activation algorithm shown in FIG. 12.

Referring to FIG. 14, an exemplary set of training data used in the back-propagation neural network technique is provided. The first training set has first six data points. The output of this run of training is compared with the seventh data point. In the second run of training, the input is the second data point to seventh data point and its output is compared with the eighth data point. All of the data points (from the first to the $380^{th}$) contain position information obtained from the motion trajectory as shown in FIGS. 7-10 and FIG. 11. The $381^{st}$ data is unknown, and can be predicted from the $375^{th}$ to the $380^{th}$ data points. In turn, other data after the $381^{st}$ data point can be generated based on a well-trained algorithm. Those values generated from the prediction will be the basis for predicting energy temporal distribution and will be used during treatment to control sonication power activation. In some applications, it is useful to continue to train the prediction algorithm by monitoring and measuring the current motion trajectory during heating treatment. The above procedure can also be illustrated by the exemplary algorithm described in FIG. 13, where the input layer 1310 now includes six input nodes and the output layer 1330 includes one output node.

3 Exemplary Systems

Figure 15:
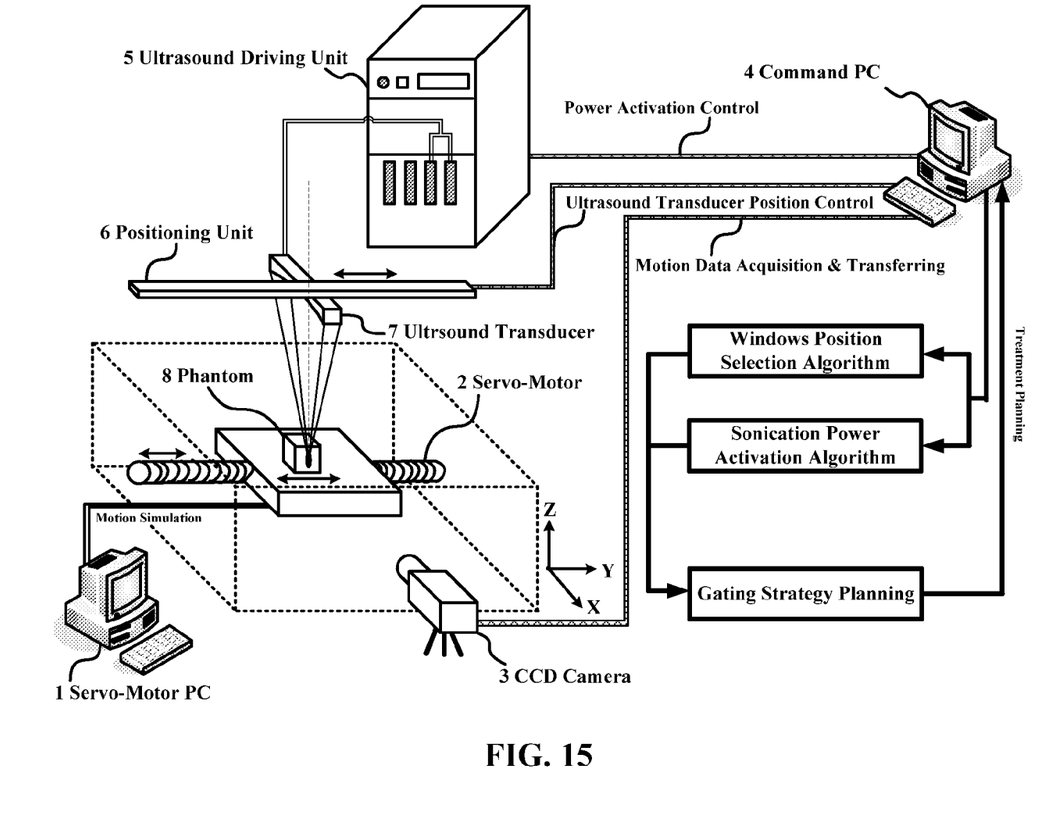
FIG. 15 is schematic diagram of a thermal therapy system according to one embodiment of the present invention.

Referring to FIG. 15, one embodiment of a thermal therapy system is shown. The system includes a servo-motor control sub-system 2, a CCD image acquisition device 3, and a high intensity focused ultrasound sub-system that includes ultrasound transducer 7. A phantom 8 is arranged on a platform controlled by the servo-motor 2 that simulates the motion effect. In designing a treatment plan responsive to respiratory motion, a window selection algorithm and a sonication power activation algorithm are used to predict the spatial and temporal distribution of energy density, respectively. The spatial and temporal energy distributions are subsequently used for determining the gating strategy.

Figure 16:
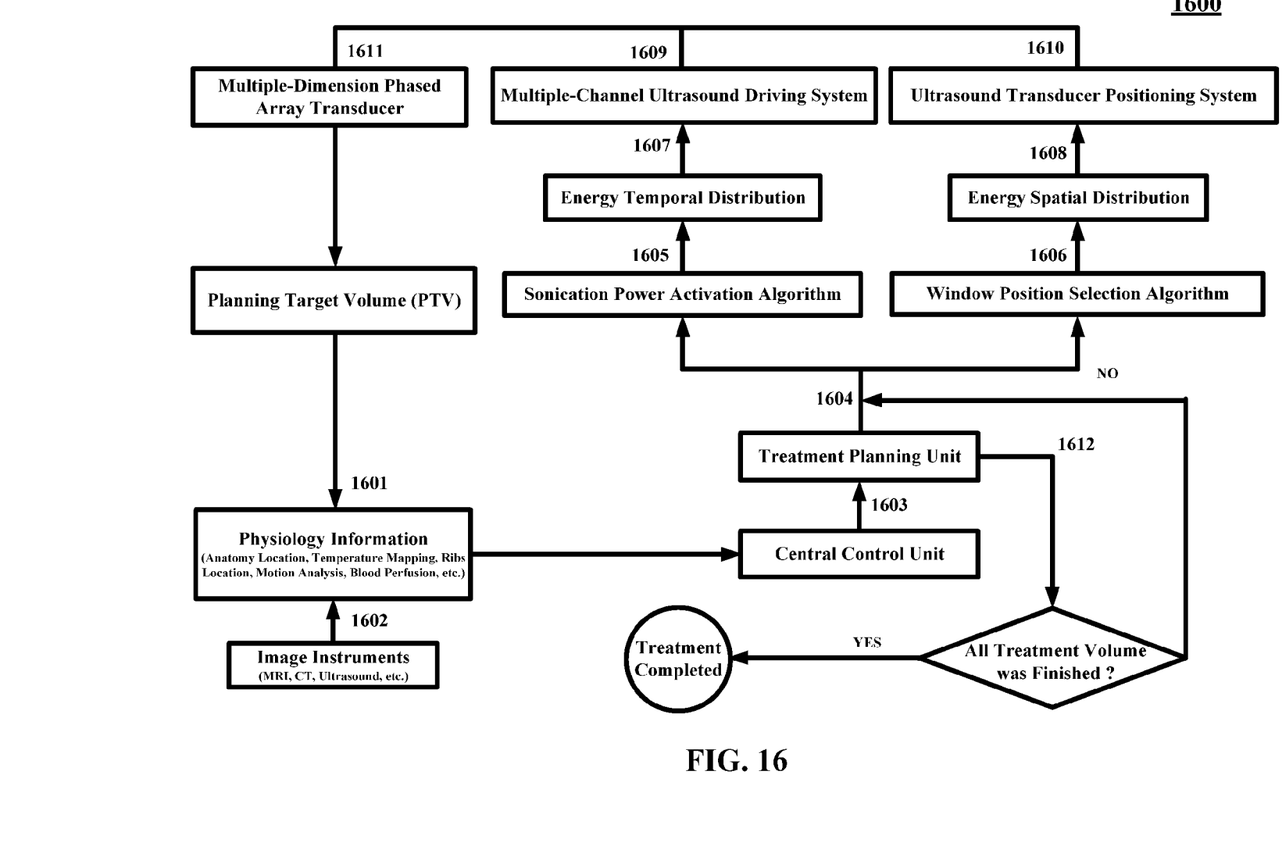
FIG. 16 is a flow diagram of a thermal therapy system according to another embodiment of the present invention.

Referring to FIG. 16, a flow chart 1600 shows the operation of another embodiment of a thermal therapy system. During a pre-treatment stage (step 1601), the system acquires physiological information of the subject of treatment, including for example, anatomical information, temperature information, ribs location, motion analysis, and blood perfusion rate. Medical image of soft tissues are then obtained from one or a combination of medical imaging techniques such as MRI, CT, ultrasound, and etc. (step 1602). Such information is provided to a central computing unit (step 1603) and further passed onto a treatment planning unit (step 1604) to determine a proper gating strategy. In some applications, the treatment planning unit can be standalone hardware or a software program implemented in the central computing unit.

The treatment planning unit develops a gating strategy for each treatment volume (e.g., each one of a plurality of GTV elements). A sonication power activation algorithm is implemented (step 1605) to predict temporal distribution of energy density (step 1607), and to control the activation of a multiple-channel ultrasound driving system (step 1609). In parallel, a window selection algorithm is used (step 1606) to estimate the spatial distribution of energy density (step 1608), and further to control an ultrasound transducer positioning system (step 1610).

During treatment, a multi-dimensional phased array transducer is controlled by both the multiple-channel ultrasound driving system and the ultrasound transducer positioning system to induce localized thermal effect at a selected treatment volume (step 1611). When a desired thermal effect is achieved at the selected volume, for example, according to the result of a real-time evaluation of psychological information and/or medical images (such as MRI-based temperature mapping), the system selects the second treatment volume and moves the transducer position accordingly. Upon completion of all treatment sessions, the thermal procedure is terminated.

A number of reference numerals in the figures have thus far not been mentioned. To comply with 37 CFR 1.84(p)(5), these numerals are mentioned as follows. In FIG. 1, the reference numeral "130" identifies a tumor. In FIG. 6, the reference numeral "609" identifies the query "Last Element?," and the reference numeral "610" identifies the step "Select Next Element." In FIG. 16, the reference numeral "1612" identifies an output of a treatment planning unit.

APPENDIX

The attached appendix contains a document which describes possible implementation of various aspects of the invention, and experimental results from working examples. The terminology used in the appendix may differ somewhat from that used herein. In the event of a conflict in terminology, that used herein is controlling. Requirements and definitions presented in the appendix are not necessarily meant to characterize the invention, but rather the specific implementations described in the appendix. The appendix includes a conference paper, which is in Ultrasonics Symposium, 2006. IEEE, pages 1734-1737. (http://ieeexplore.ieee.org/xpl/freeabs_all.jsp?arnumber=4152293)

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inducing thermal effect at a moving target, the method comprising:
receiving first data characterizing repeated motion of the moving target, the first data including data representative of a medical image of the moving target;
processing the first data to determine a treatment plan, including determining a plan for directing a signal at the moving target; and
controlling the signal directed at the moving target according to the treatment plan to induce a thermal effect, wherein the signal is activated by a power activation algorithm that includes a training algorithm configured to predict a future position of the moving target based on previously-detected positions of the moving target, the training algorithm including a network structure including at least an input layer, a hidden layer, and an output layer.

2. The method of claim 1, wherein processing the first data further includes: analyzing the first data to determine a trajectory of the repeated motion of the moving target.

3. The method of claim 2, wherein processing the first data further includes: using the trajectory of the repeated motion of the moving target to generate an estimate of energy density distribution.

4. The method of claim 2, wherein processing the first data includes: using the trajectory of the repeated motion of the moving target to determine a specification of the signal directed at the moving target.

5. The method of claim 4, wherein the specification of the signal includes one or more of the following: a location at which the signal is applied, a duration of the signal, a frequency of the signal, a magnitude of the signal, and a timing at which the signal is turned ON or OFF.

6. The method of claim 1, wherein the medical image includes a MRI and/or CT image.

7. The method of claim 1, wherein the signal directed at the moving target includes focused ultrasound.

8. The method of claim 7, wherein processing the first data includes: determining a size and a position of a gating window of the focused ultrasound.

9. The method of claim 8, wherein controlling the signal directed at the moving target includes: activating the signal based on a position of the moving target relative to the position of the gating window.

10. The method of claim 9, wherein the position of the moving target is detected by a prediction of energy temporal distribution of the focused ultrasound.

11. The method of claim 1, further comprising:
receiving second data characterizing the repeated motion of the moving target during application of the treatment plan;
wherein the signal directed at the moving target is controlled based at least in part on a result of processing the second data.

12. The method of claim 11, wherein the second data includes a medical image of the moving target.

13. The method of claim 12, wherein the medical image includes a MRI and/or CT image.

14. The method of claim 1, wherein the repeated motion of the moving target includes respiratory motion.

15. The method of claim 1, wherein controlling the signal directed at the moving target includes:
applying a first set of signals at a first element of the moving target to induce a thermal effect on the first element;
evaluating the thermal effect on the first element; and
when the thermal effect on the first element satisfies a predetermined criterion, terminating application of the first set of signals on the first element.

16. The method of claim 15, wherein controlling the signal directed at the moving target further includes:
applying a second set of signals at a second element of the moving target to induce a thermal effect on the second element.

17. A system for inducing thermal effect at a moving target comprising:
an interface is configured for receiving a first data characterizing a repeated motion of the moving target, the first data including data representative of a medical image of the moving target;
a processor is configured for determining a treatment plan according to the first data, the treatment plan including a plan for directing a signal at the moving target; and
a controller is configured for receiving the treatment plan and for controlling the signal directed at the moving target to induce a thermal effect according to the treatment plan, the controller being configured to activate the signal according to a power activation algorithm that includes a training algorithm configured to predict a future position of the moving target based on previously-detected positions of the moving target, the training algorithm including a network structure including at least an input layer, a hidden layer, and an output layer.

18. The system of claim 17, further comprising a source for generating the signal.

19. The system of claim 18, wherein the source includes a multi-channel ultrasound system.

20. The system of claim 18, wherein the signal includes focused ultrasound, and the source includes an ultrasound transducer.

21. The system of claim 20, wherein the ultrasound transducer is a multi-dimensional phased array transducer.

22. The system of claim 17, wherein the processor is configured to analyze the first data to determine a trajectory of the repeated motion of the moving target.

23. The system of claim 22, wherein the processor is further configured to estimate an energy density distribution based on the trajectory of the repeated motion of the moving target.

24. The system of claim 23, wherein the processor is further configured to determine a position of a gating window of the signal directed at the moving target based on the energy density distribution.

25. The system of claim 17, wherein the first data includes a medical image of the moving target, and the processor is configured to analyze the first data to estimate an energy density distribution.

26. The system of claim 25, wherein the processor is further configured to determine a position of a gating window of the signal directed at the moving target based on the energy density distribution.

27. The system of claim 17, further comprising a data acquisition system for detecting a position of the moving target during application of the treatment plan.

28. The system of claim 27, wherein the data acquisition system is configured to generate a medical image for detecting the position of the moving target.

29. The system of claim 28, wherein the data acquisition system includes a MRI system.

30. The system of claim 28, wherein the data acquisition system includes a video camera system.

31. The system of claim 7, wherein the controller is configured to activate the signal based on a relative position of the moving target with respect to the gating window.

32. The system of claim 28, wherein the controller is configured to evaluate the thermal effect based on the medical image generated by the data acquisition system.

33. The system of claim 17, wherein the repeated motion of the moving target is induced by physiological movement of the moving target.

34. The system of claim 33, wherein the physiological movement of the moving target includes respiratory motion.

* * * * *